US00PP11089P

United States Patent [19]

Moore

[11] Patent Number: Plant 11,089

[45] Date of Patent: Oct. 12, 1999

[54] CLIMBING ROSE PLANT NAMED 'MORSTRORT'

[75] Inventor: Ralph S. Moore, Visalia, Calif.

[73] Assignee: Weeks Wholesale Rose Grower, Inc., Upland, Calif.

[21] Appl. No.: 09/056,720

[22] Filed: Apr. 7, 1998

[51] Int. Cl.[6] ..... A01H 5/00

[52] U.S. Cl. ..... Plt./109

[58] Field of Search ..... Plt./109, 114, 115, Plt./102, 101, 108, 130

*Primary Examiner*—Howard J. Locker

*Attorney, Agent, or Firm*—Christie, Parker & Hale, LLP

[57] ABSTRACT

A new variety of Climbing rose suitable for garden decoration, having flowers of irregularly striped red and pink coloration.

1 Drawing Sheet

BACKGROUND OF THE INVENTION

This invention relates to a new and distinct variety of climbing rose. The varietal denomination of the new variety is 'Morstrort'. It has as its seed parent the variety known as Dortmund and an undistributed seedling as its pollen parent.

SUMMARY OF THE INVENTION

Among the features which distinguish the new variety from other presently available and known commercial rose cultivars are the following combination of characteristics: its flowers of irregularly striped pink and red coloration, its very pointed bud shape with a moderately large prominent hypanthium, its long mostly seven leaflet leaves and its very thorny rachis underside. The plant is a spreading climbing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'Morstrort' may be asexually propagated by cuttings, budding or grafting.

COMPARISON WITH PARENTS

The new variety may be distinguished from its seed parent, 'Dortmund', by the following combination of characteristics: whereas 'Morstrort' bears flowers of irregularly striped red and pink coloration, 'Dortmund' bears flowers of an even bright red coloration with a white eye zone at the very center of the flower. 'Dortmund' bears medium sized (about 5 to about 7 cms. in diameter) single petaled flowers (about 5 to 8 petals) in large clusters, whereas 'Morstrort' bears significantly larger flowers (about 6.5 to about 8 cms. in diameter) of more double petalage (about 14 to about 18) in smaller clusters.

The new variety may be distinguished from its pollen parent, and undistributed seedling, by the following combination of characteristics: whereas 'Morstrort' has a spreading climbing mature growth habit with long canes, the pollen parent has a bushy compact mature growth habit of about 40 to about 50 cms. in height. The pollen parent bears small flowers (about 3.5 to about 5 cms. in diameter) of irregularly striped red and white coloration, 'Morstrort' bears significantly larger flowers (about 6.5 to about 8 cms. in diameter) of irregularly striped pink and red coloration.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition ae employed.

DESCRIPTION OF THE NEW VARIETY

The following description is of rose plants of the new cultivar grown outdoors in Upland, Calif. in the month of October. Phenotypic expression my vary with environmental, cultural and climatic conditions, as well as differences in conditions of light and soil. The pattern of the striping on the under surfaces of the petals differs from the pattern of striping on the upper surfaces of the petals.

FLOWER

The new variety sometimes bears its flowers singly, usually in clusters of five or more per stem. Flowers are borne in regular rounded to somewhat flat clusters on normal medium to long stems (about 20 to about 28 cms.). Outdoors, the plant blooms abundantly and nearly continuously during the growing season. The flowers have a slight fruity fragrance.

BUD

The peduncle is about 2.2 to about 3.4 cms. in length, of average to heavy caliper, and usually erect. It is moderately rough, with many stipitate glands and small prickles. Peduncle color is between 144B and 146B.

Before the calyx breaks, the bud is about 1.2 to about 1.5 cms. in diameter at the widest point, about 1.7 to about 2.3 cms. in length, and very pointed to somewhat ovoid with a moderately large somewhat elongated hypanthium. The surface of the bud bears many stipitate glands and hairs, usually with slender entire foliaceous parts extending beyond the tip of the bud about ¼ or more of its length. Bud color is between 144A and 146B.

The inner surface of the sepals is covered with fine wooly tomentum; sepal margins are edged with some stipitate glands, numerous hairs and sometimes with a few slender entire foliaceous parts.

As the petals open (after the calyx breaks), the bud is about 1.7 to about 2.1 cms. in diameter at the widest point, about 2.4 to about 2.9 cms. in length, and very pointed to nearly urn-shaped in form. The color of the under surfaces of the newly opened petals in irregularly striped and flecked from as dark as between 60C and 53D to as light as between 62C and 54D. At the point where the petal attaches, there is a somewhat large zone of near 4B. The color of the upper surfaces of the newly opened petals is irregularly striped and flecked from as dark as between 60A and 53A to as light as between 62A and 54B. At the point where the petal attaches, there is a moderatly large zone of near 4A.

BLOOM

When fully open, the bloom ranges from about 6.5 to about 8 cms. in diameter. Petalage is semi-double to double with about 14 to 18 petals and about 1 to 3 petaloids arranged regularly. When partially open, the bloom form is somewhat high centered to cupped and the petals are loosely spiraled to cupped with petal edges somewhat reflexed outward. When fully open, the bloom form is more flat to moderately cupped, and the petals are moderately flat to undulated with petal edges less reflexed outward.

PETALS

The substance of the petals is somewhat heavy and of medium thickness, with upper surfaces somewhat velvety and under surfaces somewhat shiny to satiny. The outer petals are nearly round to broadly obovate in shape with rounded apices. The inner petals are more broadly obovate in shape with rounded apices.

NEWLY OPENED FLOWER

The under surface of the outer, intermediate and inner petals is irregularly striped and flecked from as dark as between 60C and 53D to as light as between 62D and 56C. At the point where the petal attaches, there is a somewhat large zone of near 4C. The upper surface of the outer, intermediate and inner petals is irregularly striped and flecked from as dark as between 60B and 53B to as light as between 63B and 55B. At the point where the petal attaches, there is a moderately large zone of near 4B.

The general tonality of the newly opened flower is irregularly striped and flecked from as dark as between 60B and 53B to as light as between 63B and 55B.

THREE DAY OLD FLOWER

The under surface of the outer and inner petals is irregularly striped and flecked from as dark as between 60D and 53D to as light as between 62D and 56C. At the point where the petal attaches, there is a moderately small zone of near 155A. The upper surace of the outer and inner petals is irregularly striped and flecked from as dark as between 60C and 53C to as light as between 63B and 55B. At the point where the petal attaches, there is a moderate sized zone of near 155A.

The general tonality of the three day old flower is irregularly striped and flecked from as dark as between 60C and 53C to as light as between 63B and 55B.

On the spent bloom, the petals usually drop off cleanly.

In October in Upland, Calif., blooms on the plant growing outdoors generally last about four to five or more days. Cut roses from plants grown outdoors and kept at normal indoor living temperatures generally last about four to five or more days.

MALE REPRODUCTIVE ORGANS

Stamens are average to many in number (approximately 110) and are arranged regularly about the pistil. The filaments are of moderately long length, most with anthers. Filaments are near 4A in color. The anthers are moderately large for the class and all open approximately at the same time. Anther color is near 15C when immature and near 166A at maturity. Pollen is very abundant and near 11B in color.

FEMALE REPRODUCTIVE ORGANS

Pistils vary in number (approximately 45). The styles are mostly even, moderately long in length, somewhat thin to average in caliper, and loosely bunched. Stigma and style color is between 2C and 4C. Ovaries are usually all enclosed in the calyx.

Hips are of average length, somewhat globular in shape and near 26B in color when ripe. The hip surface is usually smooth with moderately thick fleshy walls. The sepals fall away soon. Hips contain approximately 8 to 14 medium to large seeds.

FOLIAGE

The compound leaves are usually comprised of three to seven leaflets and are borne abundantly. The leaves are about 7.5 to about 12 cms. in length and about 6 to about 9 cms. in width at the widest point, moderately heavy to somewhat leathery in texture, and glossy in finish. The leaflets are about 1.5 to about 5.5 cms. in length and about 2 to about 3.3 cms. in width at the widest point, oval in shape with acute to somewhat acuminate apices and moderately acute to rounded bases. Their margins are usually simply serrate.

The upper and under surface of the mature leaf is between 137A and 139A. The under surface of the mature leaf is between 147B and 139B. The upper surface of the young leaf is between 144A and 137B, sometimes lightly suffused at the leaf margin with near 183B. The under surface of the young leaf is between 144A and 137C, sometimes moderately suffused over the full undersurface with near 183B.

The rachis is average to heavy in caliper and somewhat rough. The upper side is moderately grooved with some fine hairs and stipitate glands on the edges of the grooves. The under side of the rachis is somewhat smooth with very few fine hairs and numerous small prickles of irregular size. Prickle shape and coloration is similar to those on the branches.

The stipules are about 1.8 to about 2.3 cms. in length; of medium width; and with somewhat narrow, medium length straight points that usually turn out at an angle of more than 45 degrees. Stipules are edged with numerous stipitate glands.

The plant displays an above average degree of resistance to powdery mildew and rust as compared to other commercial varieties grown under comparable conditions in Upland, Calif.

GROWTH

The plant has a climbing spreading mature growth habit with long canes of about 180 to about 250 cms. in length. It displays moderately vigorous growth with full branching and the canes are of medium caliper.

The color of the major stems is between 137D and 147B. They bear many large prickles which are about 0.7 to about 1 cms. in length. The large prickles are almost straight, often angled moderately downward with a medium length narrowly oval base; prickle color is near 164A. The major stem bears few small prickles of similar shape and coloration.

The color of the branches is between 146A and 137C. They bear many large prickles which are of similar size and shape to the large prickles on the major stems; prickle color is between 160A and 162A, often suffused more at the base of the prickle with between 184C and 185B. The branches bear few small prickles of similar shape and coloration.

The color of the new shoots is between 144A and 146B often lightly suffused with near 183B. They bear many large prickles which are of similar shape to the large prickles on the major stems; prickle color is between 160A and 162A, often suffused with near 183B. The shoots bear few small prickles of similar shape and coloration.

I claim:

1. A new and distinct variety of climbing rose substantially as described and illustrated herein.

* * * * *

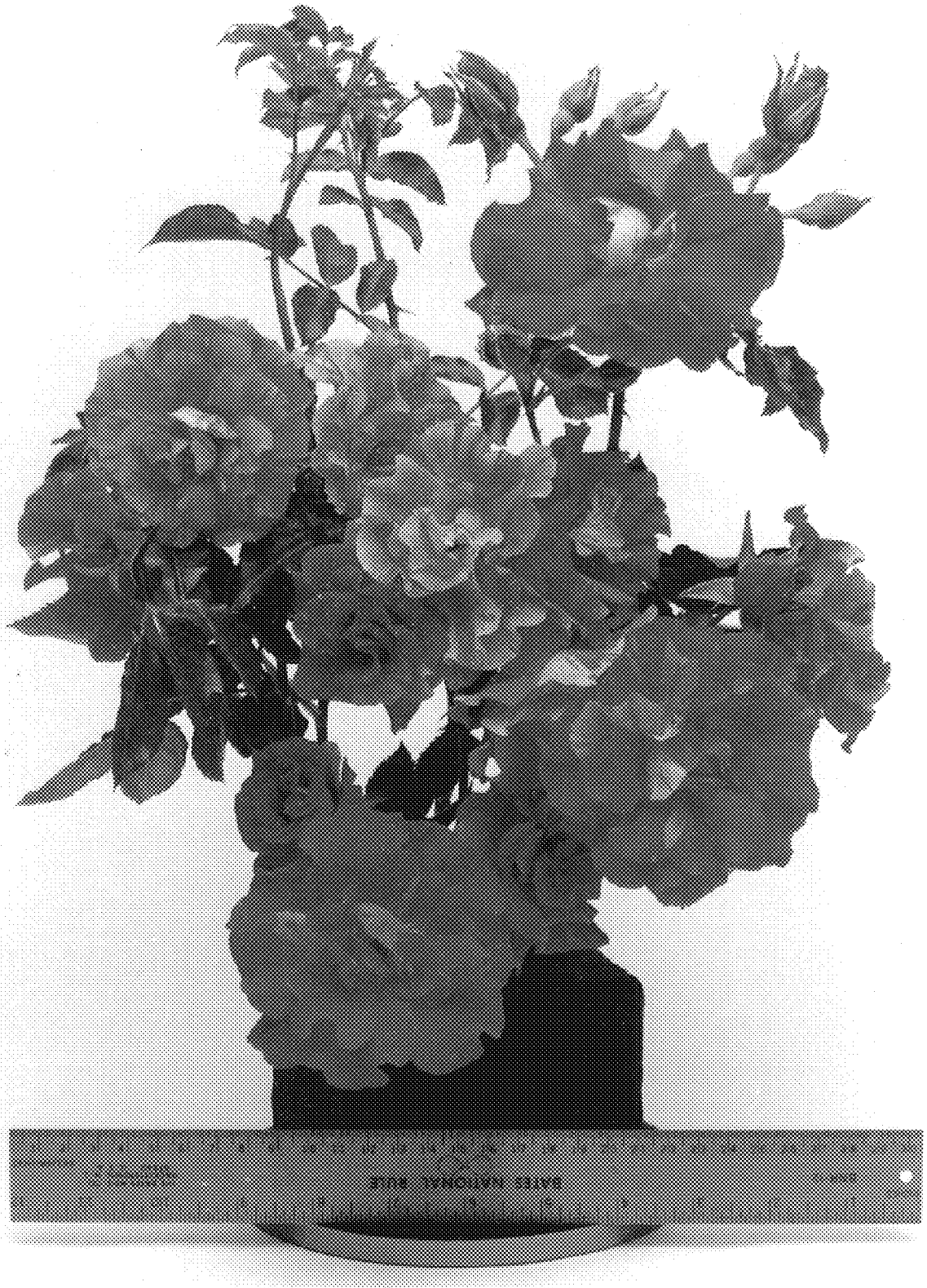

UNITED STATES PATENT AND TRADEMARK OFFICE

CERTIFICATE OF CORRECTION

PATENT NO. : PP 11,089
DATED : October 12, 1999
INVENTOR(S) : Ralph S. Moore

It is certified that error appears in the above-identified patent and that said Letters Patent is hereby corrected as shown below:

Column 6,
Line 10, the claim should read:
-- A new and distinct plant of climbing rose variety substantially as described and illustrated herein. --

Signed and Sealed this

Twentieth Day of November, 2001

*Attest:*

Nicholas P. Godici

NICHOLAS P. GODICI
*Acting Director of the United States Patent and Trademark Office*

*Attesting Officer*